United States Patent
Jones

(10) Patent No.: US 8,475,138 B2
(45) Date of Patent: Jul. 2, 2013

(54) SELF-ADAPTIVE PISTON BLOOD PUMP

(75) Inventor: Kenneth A. Jones, McKinney, TX (US)

(73) Assignee: Quest Medical, Inc., Allen, TX (US)

( * ) Notice: Subject to any disclaimer, the term of this patent is extended or adjusted under 35 U.S.C. 154(b) by 577 days.

(21) Appl. No.: 12/199,669

(22) Filed: Aug. 27, 2008

(65) Prior Publication Data

US 2009/0060753 A1 Mar. 5, 2009

Related U.S. Application Data

(60) Provisional application No. 60/968,203, filed on Aug. 27, 2007.

(51) Int. Cl.
*F04B 49/00* (2006.01)

(52) U.S. Cl.
USPC .................. 417/44.2; 417/3; 417/4; 604/152; 604/153; 92/98 R; 92/98 D

(58) Field of Classification Search
USPC ........... 417/3, 4, 42, 44.2, 63; 92/98 R, 98 D, 92/99, 136; 604/151–153
See application file for complete search history.

(56) References Cited

U.S. PATENT DOCUMENTS

| | | | |
|---|---|---|---|
| 3,911,897 A | 10/1975 | Leachman, Jr. | |
| 3,916,449 A | 11/1975 | Davis | |
| 4,034,742 A | 7/1977 | Thoma | |
| 4,611,578 A | 9/1986 | Heimes | |
| 4,687,424 A | 8/1987 | Heimes | |
| 4,769,001 A | 9/1988 | Prince | |
| 5,092,878 A | 3/1992 | Miyata | |
| 5,536,237 A | 7/1996 | Prince et al. | |
| 5,638,737 A * | 6/1997 | Mattson et al. | 92/101 |
| 5,645,531 A * | 7/1997 | Thompson et al. | 604/67 |
| RE36,386 E * | 11/1999 | Abbott et al. | 604/6.13 |
| 6,572,530 B1 | 6/2003 | Araki et al. | |
| 6,991,595 B2 | 1/2006 | Burke et al. | |
| 7,004,924 B1 * | 2/2006 | Brugger et al. | 604/6.13 |
| 7,842,003 B2 * | 11/2010 | Jones et al. | 604/6.11 |
| 2004/0186409 A1 | 9/2004 | Cavalcanti et al. | |
| 2005/0238497 A1 * | 10/2005 | Holst et al. | 417/44.2 |
| 2006/0178611 A9 * | 8/2006 | Westberg et al. | 604/6.03 |
| 2007/0073393 A1 * | 3/2007 | Kung et al. | 623/3.13 |

* cited by examiner

*Primary Examiner* — Peter J Bertheaud
*Assistant Examiner* — Dominick L Plakkoottam
(74) *Attorney, Agent, or Firm* — David W. Carstens; Kevin M. Klughart; Carstens & Cahoon, LLP

(57) ABSTRACT

A self-adjusting fluid pump that includes a piston pump containing at least one piston with a pressure sensor. The fluid pump including at least one fluid-containing pump chamber within the piston pump, adjacent to said piston, wherein advancing the piston causes fluid flow from the pump chamber to a biological destination, and retracting the piston causes fluid to passively till the pump chamber. A microprocessor, senses piston pressure to calculate the rate of fluid input flow into the pump chamber for each pump cycle. If the output flow rate deviates from the input flow rate by a pre-specified value range, the microprocessor adjusts the piston pump to match the output flow rate with the input flow rate by increasing or decreasing stroke rate (piston velocity), stroke volume, or a combination of both.

14 Claims, 11 Drawing Sheets

SELF-ADAPTIVE PISTON BLOOD PUMP

CROSS REFERENCE TO RELATED APPLICATIONS

This application claims the benefit of and priority to U.S. Provisional Patent Application No. 60/968,203 filed Aug. 27, 2007, the technical disclosures of which are hereby incorporated herein by reference.

TECHNICAL FIELD

The present invention relates generally to equipment used to deliver fluids to a patient, and more specifically to a piston pump mechanism that delivers sterile fluids for medical treatment such as cardioplegia solution during open-heart surgery.

BACKGROUND OF THE INVENTION

Extracorporeal blood pumps or in vivo heart assist devices comprise various designs, including peristaltic roller pump, centrifugal pumps, axial flow pumps, pneumatic chamber pumps, and hydraulic chamber pumps. These pumps vary widely in cost and efficacy, and their uses vary from supporting a patient on a heart/lung machine to assisting the human heart as a bridge to transplant or replacing the human heart.

One such application is long term Extracorporeal Membrane Oxygenator (ECMO) support. In this process, a heart/lung machine provides cardiopulmonary support to a patient, typically a pediatric patient, for many days. Many technical challenges are faced in providing such support. The patient is maintained in an unconscious state. Fluids must be provided to the patient via intravenous (IV) administration to sustain circulation and systemic pressure. This is a critical process, and inattentiveness by medical personnel can have serious negative consequences.

With current pumps, inadequate input volume can result in excessive negative pressures in the pump inlet conduit and the patient's venous system, which may result in air emboli entering the extracorporeal circuit via the cannulation site.

Therefore, it would be desirable to have an adaptive pump mechanism that can adjust its stroke volume and stroke rate to maintain a fluid flow rate that supports a specified blood pressure range within a patient.

SUMMARY OF THE INVENTION

The present invention provides a self-adjusting fluid pump that includes a piston pump containing at least one piston with a pressure sensor. The fluid pump also includes at least one fluid-containing pump chamber within the piston pump, adjacent to said piston, wherein advancing the piston causes fluid to flow from the pump chamber to a biological destination, and retracting the piston causes fluid to passively fill the pump chamber. A microprocessor uses data from the piston pressure sensor to calculate the rate of fluid input flow into the pump chamber for each pump cycle. If the output flow rate deviates from the input flow rate by the pre-specified value range, the microprocessor adjusts the fluid output flow of the piston pump in order to match the output flow rate with the input flow rate. The adjustment can be made by increasing or decreasing stroke rate (piston velocity), stroke volume, or a combination of both.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

DETAILED DESCRIPTION OF THE DRAWINGS

Figure 1:
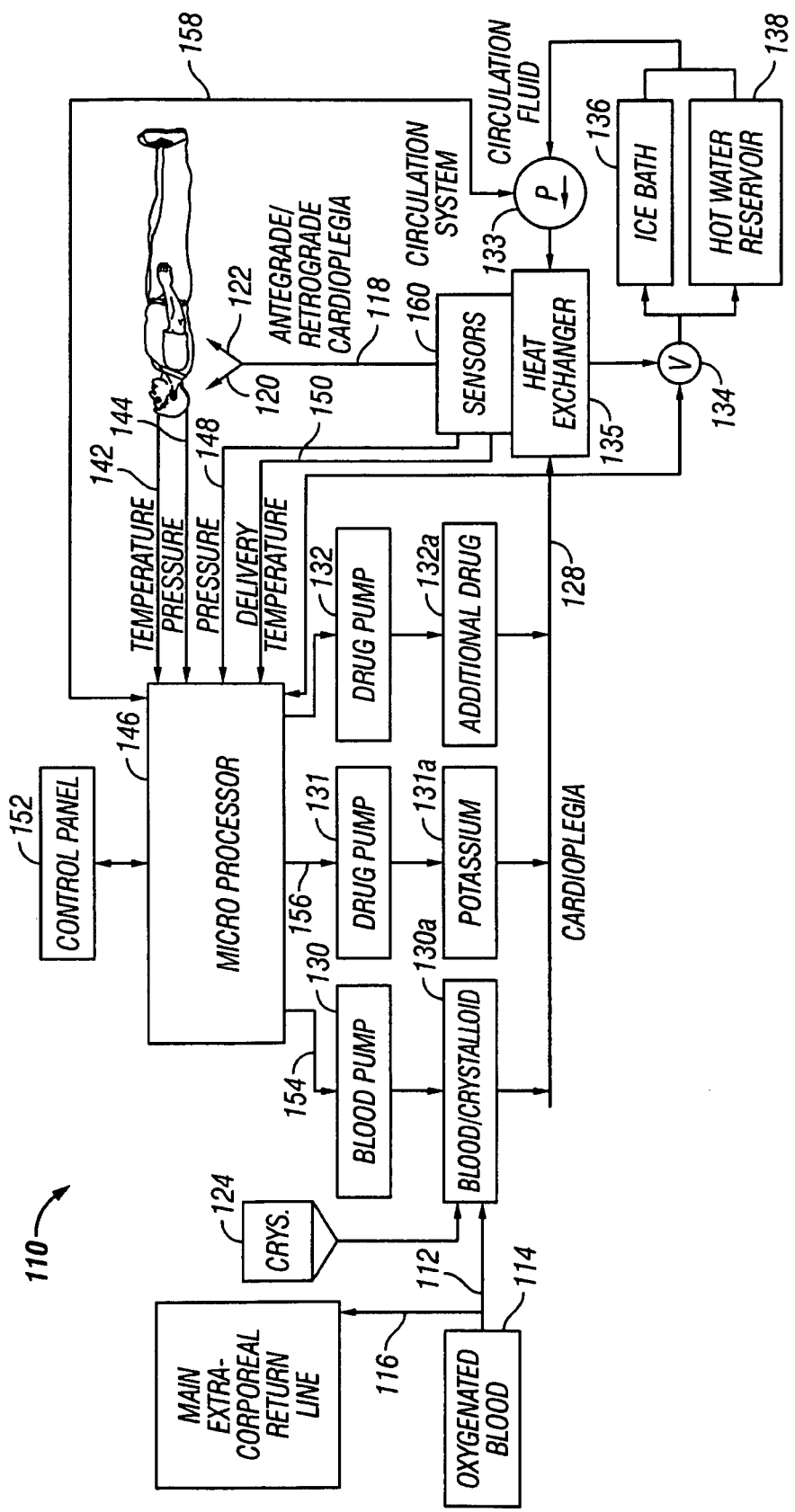
FIG. 1 is a block diagram of a cardioplegia delivery system that provides solution to the heart of a patient during open heart surgery in accordance with a preferred embodiment of the present invention.

FIG. 1 is a block diagram of a cardioplegia delivery system 110 that provides solution to the heart of a patient during open heart surgery. The principal component of the cardioplegic solution is blood delivered to the system through conduit 112, which is connected to the output of oxygenator 114 of the heart/lung machine sustaining the patient's vascular system while the heart is isolated during surgery. Oxygenator 114 provides arterial blood in the main extracorporeal circuit through a return line 116 to the patient's aorta.

A fraction of the heart/lung machine output is diverted into conduit 112 for processing by the cardioplegic circuit and forwarding to the patient's heart through cardioplegia delivery line 118. The cardioplegic solution flowing through line 118 may be delivered through antegrade line 120 to the aortic root, or through retrograde line 122 to the coronary sinus.

In the present example, a crystalloid solution is stored in container 124 for combination with blood flowing in line 112 in a disposable pumping cassette 130a. The output of cassette 130a is supplied through line 128 to a heat exchanger 135. Pump cassette 130a is controlled by an electromechanical pump mechanism 130 in which cassette 130a is mounted. A second pump 131 controls cassette 131a containing potassium solution, which supplies its output to line 128 downstream from the cassette. A third pump 132 controls cassette 132a containing any additional drug supplies.

In heat exchanger 135, the cardioplegic solution is juxtaposed with a circulating temperature controlled fluid to adjust the temperature of the solution prior to forwarding the solution to the heart through line 118. Preferably pump 133 circulates temperature controlled fluid through heat exchanger 135 either by push or pull. FIG. 1 depicts a push-through coolant system in which a pump 133 circulates the control fluid through heat exchanger 135 and then to a two-way valve 134, which valve 134 may direct the circulating fluid either to an ice bath 136 for cooling or a heated water reservoir 138 for heating. The circulating fluid is then pumped back through heat exchanger 135, where the cardioplegia solution receives heating or cooling without contamination across a sealed heat transfer material or membrane within heat exchanger 135.

The system includes patient monitoring of myocardial temperature along the signal path 142 and heart pressure along signal path 144 communicating to a central microprocessor control section 146. In addition, the pressure and temperature of the cardioplegic solution in delivery line 118 is sensed via sensors 160 and the data is forwarded along signal paths 148 and 150 to control microprocessor 146. Data input to microprocessor 146 through control panel 152 may include an advantageous combination of the following parameters: desired overall volumetric flow rate, desired blood/crystalloid ratio to be forwarded, desired potassium concentration to be established by pump 131, desired supplemental drug concentration to be established by pump 132, desired temperature of solution in cardioplegia delivery line 118, and safety parameters such as the pressure of the cardioplegia solution in the system or in the patient.

In response to the data input through the control panel 152 and the monitored conditions along signal paths 142, 144, 148 and. 150, microprocessor control section 146 controls the operation of pump mechanism 130, via signal path 154, and of potassium pump 131 by way of a signal along path 156. In addition, the microprocessor control section 146 controls the circulation of fluid in the heat exchanger circulation path along signal path 158 either for obtaining a desired patient temperature or a desired output solution temperature. Further, the safety parameters such as pressure limits for a particular procedure or a particular patient may be controlled based upon input settings or based upon preset standards, as for example, one range of acceptable pressure limits for antegrade and another range for retrograde cardioplegia.

In accordance with a preferred embodiment of the invention, microprocessor controller section 146 controls the pump mechanism 130 to combine crystalloid from container 124 and blood from line 112 in any selected ratio over a broad range of blood/crystalloid ratios. Controller 146 may command the pump mechanism 130 to deliver blood without crystalloid addition. The blood/crystalloid ratio can be adjusted from an all blood mixture to an all crystalloid mixture, with multiple ratios in between. The rate of flow produced by the pump mechanism 130 of the combined output from disposable pump cassette 126 is preferably variable from 0 to 999 milliliters per minute. Potassium pump 131 is automatically controlled to maintain a constant potassium solution concentration. In other words, if the blood pump flow rate is increased, the potassium pump flow rate is automatically increased.

Figure 2:
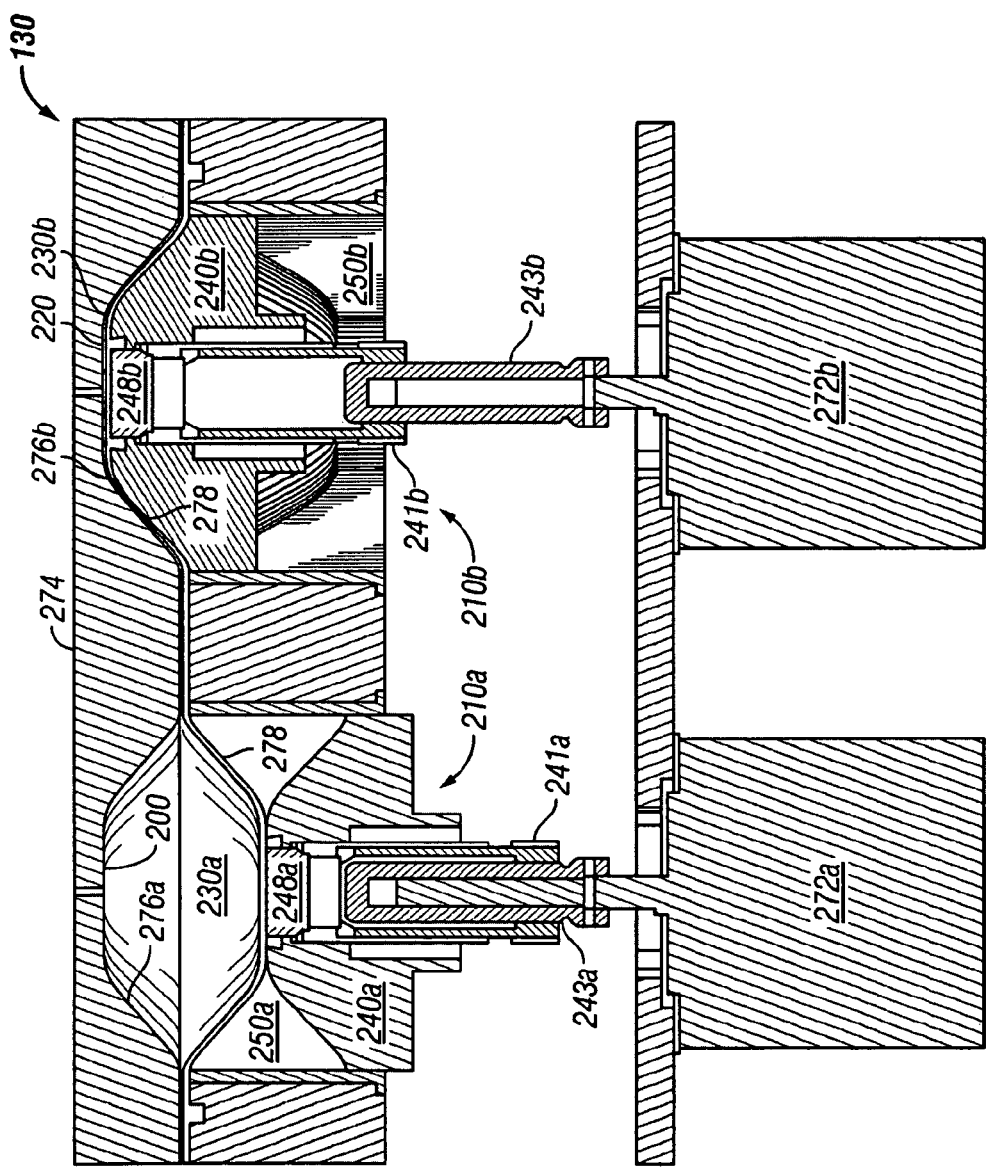
FIG. 2 is a schematic illustration of the functioning of one embodiment of a pump mechanism for use in a preferred embodiment of the present invention.

FIG. 2 illustrates one embodiment of a pump mechanism 130 for incorporation into a fluid delivery system such as that described in FIG. 1. The pump mechanism 130 operates on a flexible, disposable fluid cassette 220 which maintains the sterility of the fluid as it passes through the mechanism. The pump mechanism 130, as described herein, features two piston assemblies 210a, 210b. The piston assembly 210 of the present invention enables the mixing of multiple fluids in consistent, accurate ratios, and the delivery of such mixture at a definable, consistent volumetric flow rate. A fluid delivery system incorporating the present invention may have multiple applications within the medical industry and, in particular, applications in at least the areas of intravenous fluid delivery, limb perfusion, organ perfusion and cardioplegia delivery. Notwithstanding the foregoing, the present invention is adaptable to be incorporated into any variety of fluid delivery systems, whether medical related or not, and scalable to provide a large range of volumetric flow rates.

Figure 3:
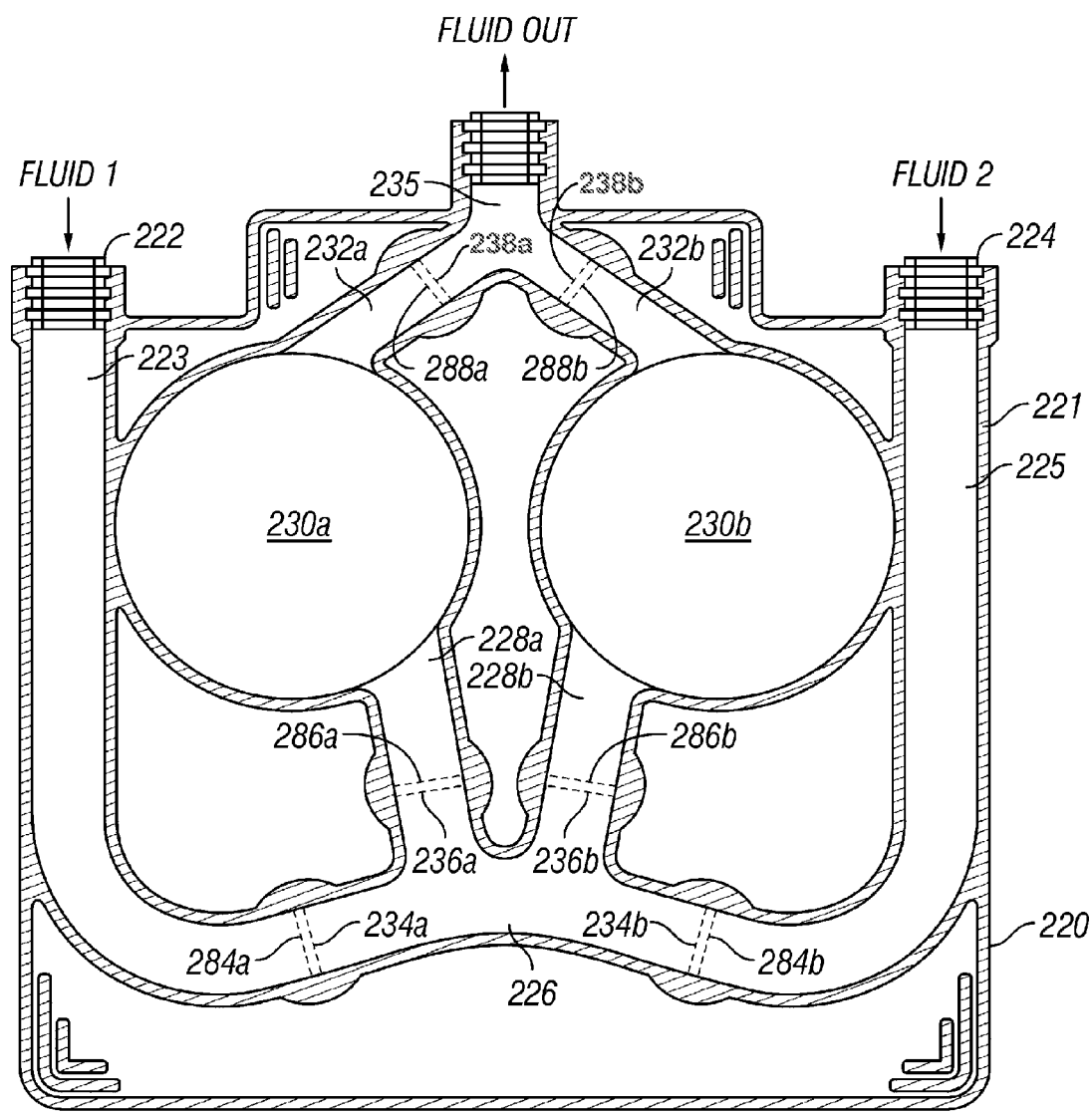
FIG. 3 is a plan view of one embodiment of a disposable fluid cassette for the pump mechanism of FIG. 2.

FIG. 3 illustrates one embodiment of a disposable fluid cassette 220. The cassette 220 may be formed from two thin, flexible sheets of material, such as polyvinylchloride. The sheets are bonded together along a selected bond area 221 to form particularized open flow paths and chambers. Any number of techniques (as an example, RF welding) may be employed for such bonding. The thickness of the material should be such that variations which occur during manufacture should not significantly affect the volumetric accuracy of the fluid output of the pump mechanism 130.

The cassette 220 includes a first fluid inlet 222 and a second fluid inlet 224. In a preferred embodiment, the first fluid inlet 222 accommodates blood and the second fluid inlet accommodates a crystalloid fluid typically used during open heart surgery. Fluid entry paths 223, 225 run respectively from inlets 222, 224 to a common inlet path 226, which bifurcates to form inlet flow paths 228a and 228b. Inlet flow paths 228a and 228b respectively terminate in pump chambers 230a, 230b.

Outlet paths 232a, 232b, forming the respective output pathways from pump chambers 230a, 230b, join at a common outlet path 235. The outlet path 235 is the gateway for passage of the first and second fluid mixture to other portions of the fluid delivery system.

Figure 4:
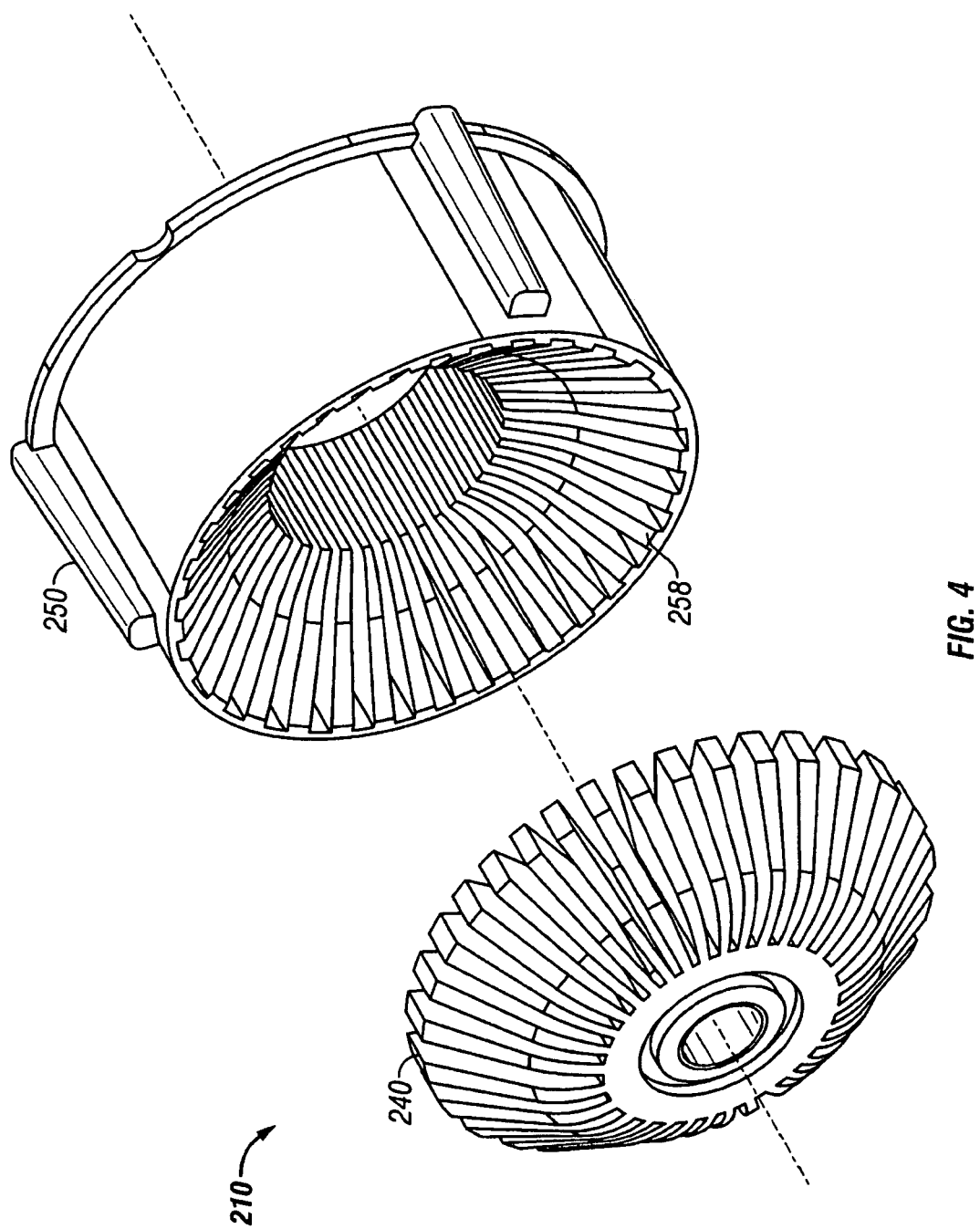
FIG. 4 is an exploded, perspective view of a piston assembly in accordance with a preferred embodiment of the present invention.
Figure 5:
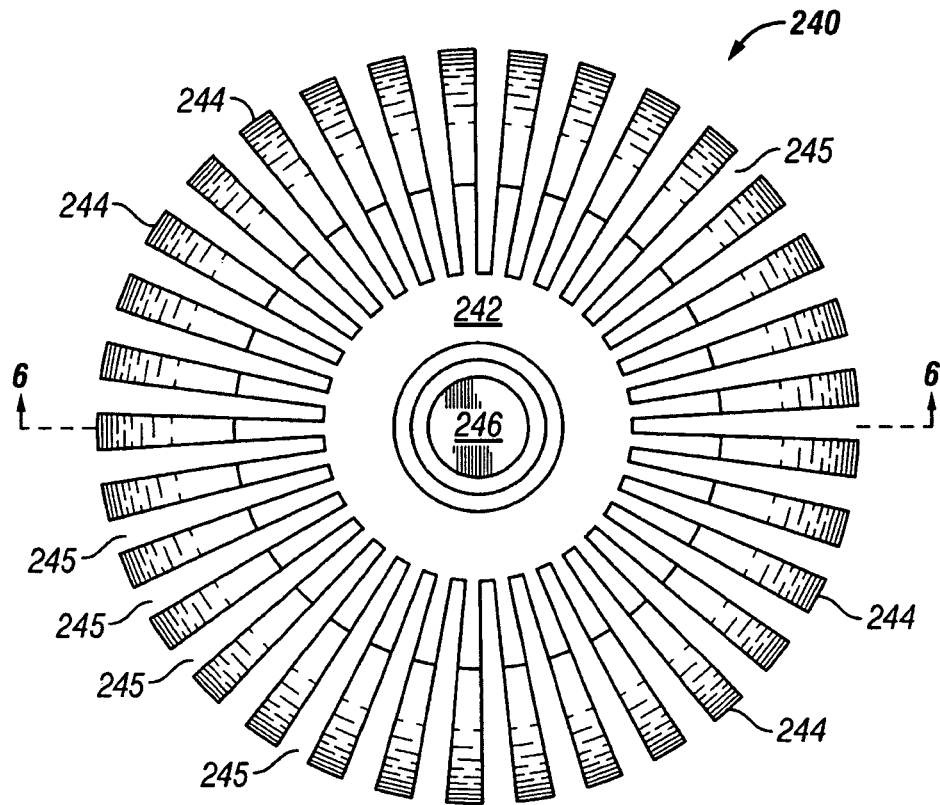
FIG. 5 is a plan view of the piston of the piston assembly of FIG. 4.
Figure 6:
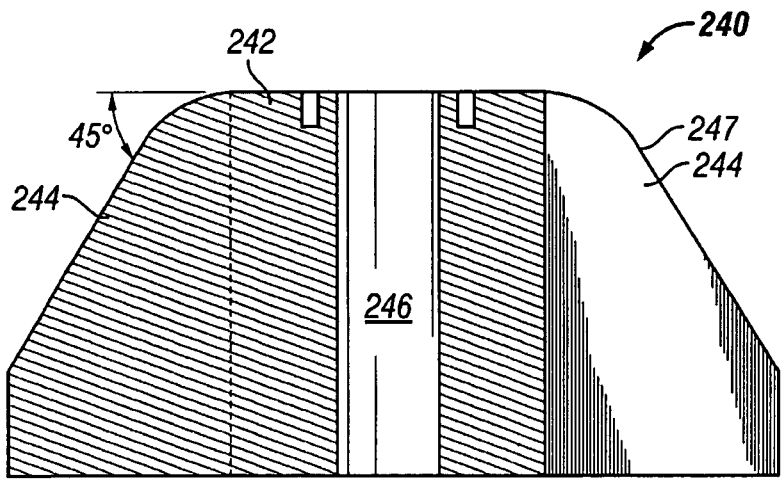
FIG. 6 is a sectional view of the piston along line 6-6 of FIG. 5.

FIG. 4 illustrates the piston assembly 210 of FIG. 2. The piston assembly 210 has a piston 240 and a base 250, such base 250 being dimensioned to operatively receiving the piston 240. As shown in FIGS. 5 and 6, piston 240 includes a central hub 242 with a plurality of splines 244 extending outwardly therefrom. The plurality of splines 244 are integrally formed with the hub 242 and, extend radially outward. The piston 240 generally forms a convex supporting surface 247, wherein each spline 244 progresses from, a full height at the hub 242 to a substantially lesser height at the perimeter of the piston 240. In the preferred embodiment, the angular displacement of the supporting surface 247 corresponds, although in a differing direction of displacement, to an angular displacement of a facial surface, or receiving surface 258, of the base 250.

Figure 10:
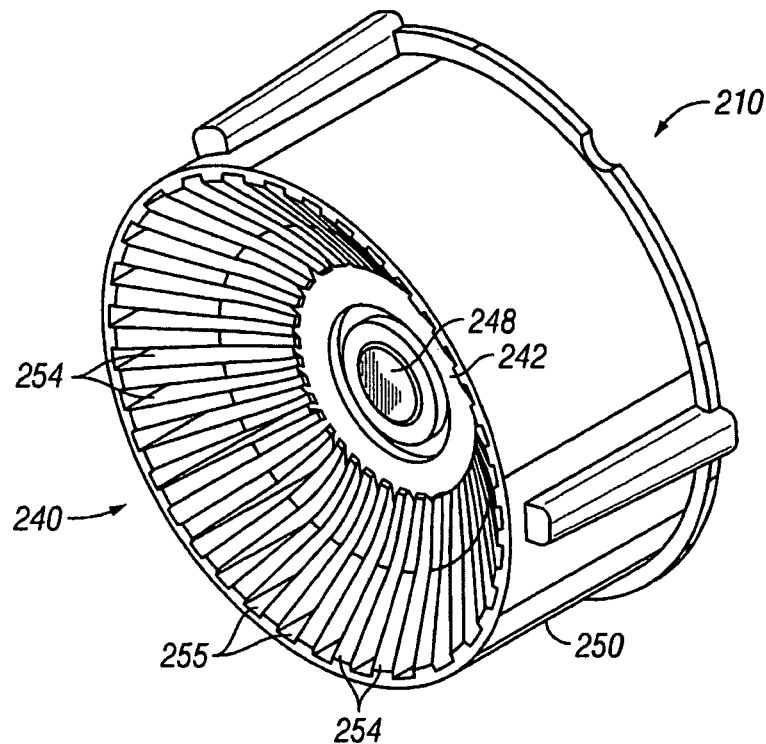
FIG. 10 is a perspective view of the piston assembly of FIG. 4 in a fully retracted state.

Referring to FIG. 5, the hub 242 can include a passage 246 extending through the piston 240, such passage 246 extending along an axial centerline of the piston 240. In the preferred embodiment, the passage 246 receives and carries a contact pressure sensor 248 (see FIGS. 10 and 11). The incorporation of a pressure sensor 248 in the piston 240 permits monitoring of a fluid pressure within a pumping chamber associated with piston 240. Consequently, the intrachamber fluid pressure is useful in determining:

1. The volumetric content of pumping chamber 230,
2. The presence of non-occluding valves adjacent pump chamber 230, and
3. The presence of excessive fluid delivery pressures as well as excessive back-pressures presented to pump mechanism 130.

Figure 7:
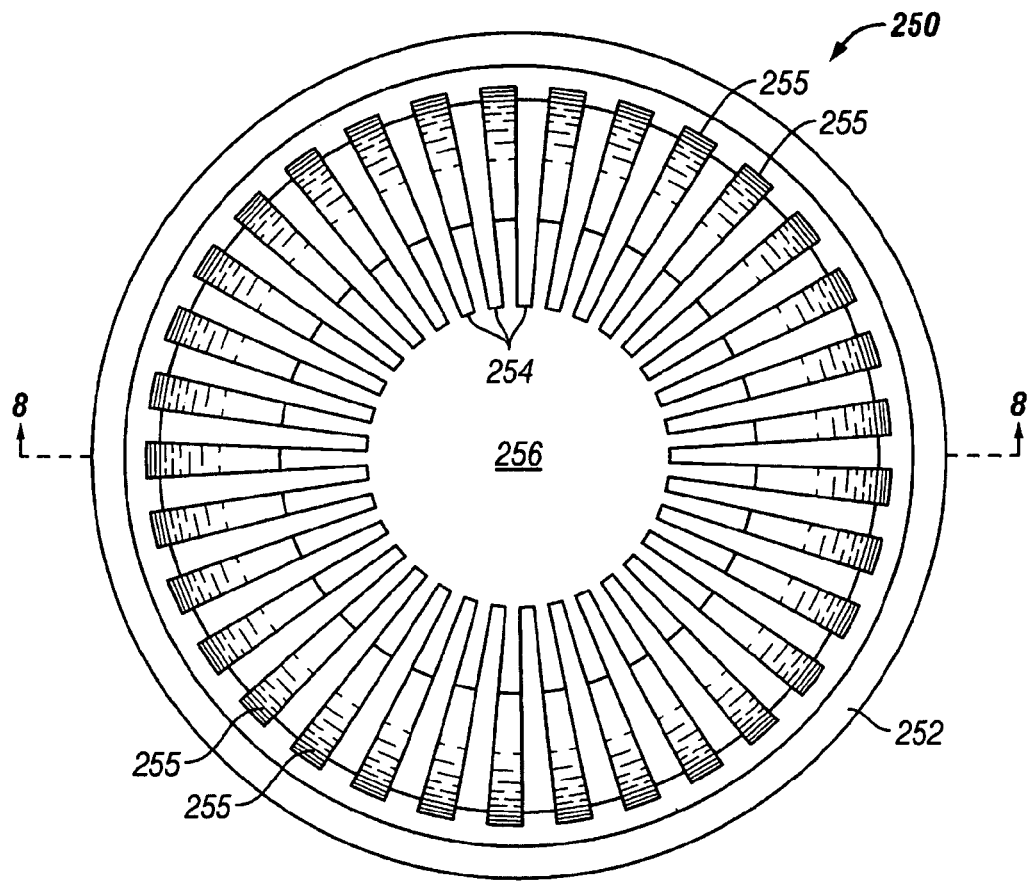
FIG. 7 is a plan view of the base of the piston assembly of FIG. 4.
Figure 8:
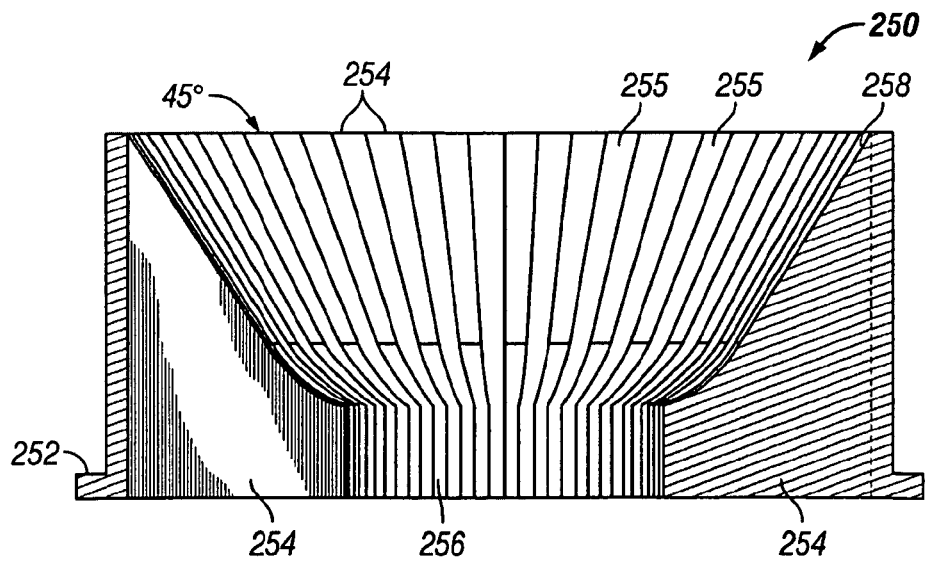
FIG. 8 is a sectional view of the base along line 8-8 of FIG. 7.

As shown in FIGS. 7 and 8, the base 250 includes a collar 252 and a plurality of ribs 254. The plurality of ribs 254 are integrally formed with collar 252 and extend radially inward to define a central passageway 256. The base 250 is constructed so as to (i) permit the hub 242 to be movably received by the central passageway 256 and (ii) allow the plurality of splines 244 to be movably interposed between the plurality of ribs 254 (see FIGS. 10 and 11). As shown in FIG. 8, the ribs 254 generally form a concave receiving surface 258 which inversely complements the convex supporting surface 247 of the piston 240. Accordingly, each rib 254 progresses from a full height at the collar 252 to a substantially lesser height at the perimeter of central passageway 256. In the preferred embodiment, the angular displacement of the receiving surface 258 is substantially 45 degrees. Further, the angular displacement of the supporting surface 247 of the piston 240 is substantially equivalent.

In the preferred embodiment, each spline 244 has a thickness substantially equal to that of each rib 254. Therefore, when the base 250 receives the piston 240 there exists limited and tightly controlled clearance between any rib-spline interface, thereby preventing the opportunity for the cassette material to become pinched or positioned between the elements during operation. The piston 240 may be manufactured from a lubricated material such as acetyl fluoropolymer (for example, Delrin AF from DuPont, Co., Wilmington, Del.), and the base 250 from a glass reinforced polycarbonate (for example, a 10% glass material Lexan 500 from GE Plastics, Pittsfield, Mass.), to permit largely unrestricted motion of the piston 240 relative to the base 250 despite the potential for repeated contact between two elements. The number of splines 244 and ribs 254 should be such that the space 245 between each spline 244 and the space 255 between each rib 254 (such being substantially equivalent if the thickness of each spline 244 is substantially equivalent to the thickness of each rib 254) is of such a distance to enable the adjacent splines (or ribs as the case may be) to support the cassette 220 across the spaces 245, 255.

The complementary shaping of the piston 240 and the base 250 enables a resting cassette pumping chamber 230 to be supported by a constant surface area throughout an entire stroke of the piston 240, thereby foreclosing the opportunity for the cassette material to be stretched, unsupported or pinched during movement of the piston 240. Furthermore, the geometric relation between the elements permits a mathematical relation to be established. In the preferred embodiment, for example, the diameter of the piston 240 linearly decreases, relative to the interior of the pumping chamber 230, with the retraction of piston 240. A similar relation exists for the advancement of piston 240. Thus, during retraction of the piston 240, an enclosed volume is created which increases as a quadratic function of the piston's 240 movement. The relation can be used to maintain a constant fluid flow rate because the rate of piston movement can be controlled to achieve a predetermined flow rate.

Although the preferred embodiment defines a base 250 having a receiving surface 258 with a 45-degree angular displacement along the plurality of ribs 254, the angular displacement may measure from 30 to 60 degrees. Notwithstanding, the preferred embodiment ensures:
  (i) a relatively significant pumping chamber volume,
  (ii) full support of the cassette pumping chamber 230 through an entire pumping stroke, and
  (iii) avoidance of trapped air within the pumping chamber 230.

Figure 9:
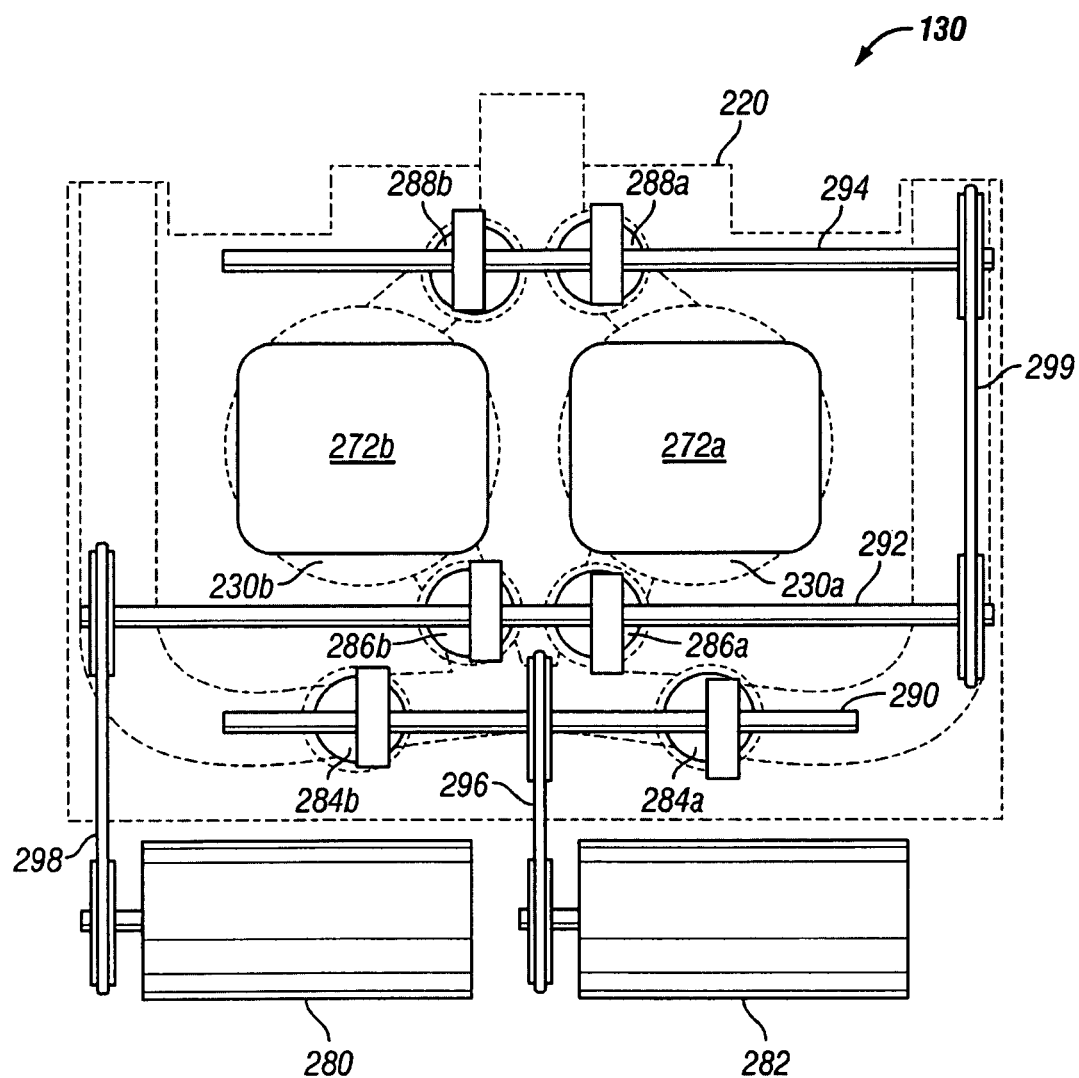
FIG. 9 is a view from beneath a pump mechanism which accommodates the disposable fluid cassette of FIG. 3.

FIG. 9 is a rear view of the elements of the pumping mechanism 130 which accommodates the cassette 220 of FIG. 3 (an outline of the cassette 220 is provided). The pumping mechanism 130 incorporates a pair of stepper motors, or pumping motors 272a, 272b. The pumping motors 272a, 272b rotationally engage, through attached lead screws 243a, 243b, a threaded portion 241a, 241b of each piston 240a, 240b (see FIG. 2). Two drive motors 280, 282 control the operation of the mechanism's valves. Drive motor 280 engages cam shaft 292 (such driving inlet valves 286a and 286b) through a timing belt 298. Drive motor 280 also engages cam shaft 294 (such driving outlet valves 288a and 288b) through a timing belt 299 which rotationally couples cam shafts 292 and 294. Drive motor 282 engages cam shaft 290 (which drives inlet valves 284a and 284b) through an independent timing belt 296.

Referring to both FIGS. 3 and 9, the interrelation of the pumping mechanism 130 and the fluid mixing operation are better illustrated. In short, mixing of a first and a second fluid, for the purposes of the illustrated embodiment, is accomplished through the continuous introduction of a first and a second fluid into multiple pumping chambers in a predefined, systematic pattern. The pumping mechanism 130, through the operation of a series of valves, controls the flow of fluid throughout the cassette 220. Specifically, a valve, if actuated, presses the first and second sheets of the cassette 220 together at a cassette valve location to occlude the valve location's corresponding flow path.

For pumping mechanism 130, inlet valves 284a, 284b, 286a, 286b control the introduction of fluid into the pumping chambers 230a, 230b. The inlet valves 284a, 284b, 286a, 286b act on the cassette 220 at valve locations 234a, 234b, 236a and 236b, respectively. Outlet valves 288a, 288b control the flow of fluid from the pumping chambers 230a, 230b by acting on cassette valve locations 238a, 238b.

As an example, in preparation of filling pumping chamber 230b, valve 286a (valve location 236a) is actuated to close inlet flow path 228a, while valve 288b (valve location 238b) also occludes outlet path 232b to permit the accumulation of fluid within the pumping chamber 230b. During filling, valves 284a, 284b and 286b (valve locations 234a, 234b and 236b, respectively) open and close in a predetermined synchronized pattern to permit a ratio of the first and second fluids to enter the pumping chamber 230b. Upon completion of the fill, valves 286b and 288a respectively occlude flow paths 228b and 232a, and valve 288b is de-actuated to permit fluid to flow from the pumping chamber 230b. Fluid movement, whether filling or being expelled from the pumping chambers 230a, 230b, is initiated through the movement of the mechanism's pump assemblies 210a, 210b.

Referring back to FIG. 2 and the operation of the pump mechanism 130, a fastened retaining door 274 tightly constrains the cassette 220 against the upper surface of the pump mechanism. The retaining door 274 possesses a number of cavities 276a, 276b, the number corresponding to the number of pump assemblies included within the pump mechanism 130. The cavities 276a, 276b are complementary of and can fully receive at least a portion of the pistons 240a, 240b when they are in a fully advanced position. Accordingly, the conformance of the cavities 276a, 276b to the shaping of the pistons 240a, 240b enables the expulsion of substantially all the fluid from the pump chambers 230a, 230b for a full piston stroke. Complete fluid displacement makes such pumping mechanism 130 and its methodology suitable for single pumping stroke applications.

When the cassette 220 is operatively positioned in the pump mechanism 130, the cassette pumping chambers 230a, 230b align with and rest upon the pump assemblies 210a, 210b. The retaining door 274 effectively constrains the cassette 220 during operation. The formed volume of the paths and chambers of the cassette 220 may be slightly greater or less than the nominal constraining volume defined by the rigid constituents of the pump mechanism 130. Practically, the firm restraints of the pump mechanism 130 permit the development of relatively high fluid pressures within the cassette 220 without significant or detrimental deformation of the cassette material. Indeed, constraining the cassette 220 over effectively the entire cassette surface creates an inherently non-compliant system. Such non-compliance contributes to the ability of the pump mechanism 130 to produce consistent, accurate volumetric fluid delivery.

In the preferred embodiment, the cassette pumping chambers 230a, 236b do not rest directly upon the supporting surfaces of the piston 240 and/or base 250. Instead, a resilient material 278, attached about the upper portion of the base 250, operates to conform to the supporting surface of the piston assembly 210 without regard to whether the piston 240 is fully advanced, retracted or in some intermediate position. The resilient material 278 protects the pump mechanism 130 from fluid intrusion in the event any liquid is spilled on the device operational environment. The resilient material 278 also acts to further protect the cassette 220 from damage that could inadvertently occur through the operation and movement of the piston assembly 210.

In an alternative embodiment, the resilient material 278 could include reinforcement means to provide additional rigidity to the resilient material 278. As an example, reinforcement means could include a fine metal mesh or cloth embedded within the material used to fabricate the resilient material 278. Alternatively, the resilient material 278 could include a spiral wire which is capable of concentric expansion to provide facial and lateral support for a resting cassette 220 about the interior of the base 250 (when piston 240 is in a retracted position) or about the piston 240 (when piston 240 is in an advanced position). Lastly, the material 278 could be formed of cloth altogether to eliminate any elasticity. This alternative embodiment, and its variations, could permit the use of fewer rib/splines or provide greater reliability in applications that require the piston assembly 130 to operate in larger applications, in the presence of greater fluid pressures or both.

Figure 11:
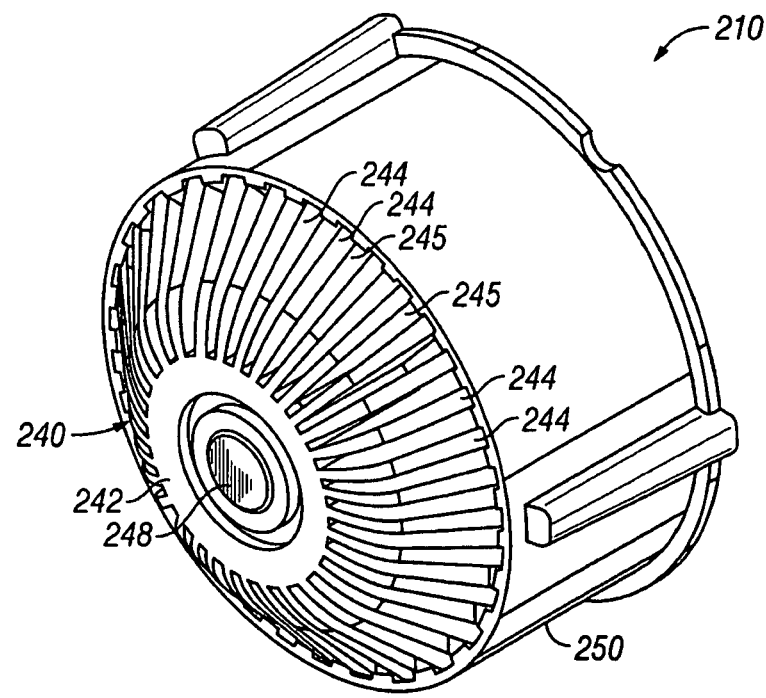
FIG. 11 is a perspective view of the piston assembly of FIG. 4 in a fully advanced state.

In FIG. 2 piston 240a is fully retracted (see also FIG. 10) and piston 240b is fully advanced (see also FIG. 11). Relative to fluid displacement, pump chamber 230a would be substantially full of fluid, and pump chamber 230b would have just expelled its contents. For the present embodiment, the pump mechanism 130 can deliver substantially continuous fluid flow through the sequential filling and expulsion of fluid from the pumping chambers 230a, 230b.

In addition to providing substantially continuous flow, the pump mechanism 130 of the present embodiment incorporates a four-step filling protocol, which is in parallel to the expulsion of fluid from the other pump chamber, to ensure the volumetric accuracy of the delivered fluid. First, valve 288a is actuated and a first fluid is introduced into the pumping chamber 230a through the synchronized operation of the inlet valves. The pump motor 272a retracts a predefined amount to admit a volumetric quantity of the first fluid that, relative to the total volume of the pumping chamber 230a, satisfies a predefined fluid mixture ratio. Second, the system tests the volumetric accuracy of the first fluid within the pump chamber 230a. As a prelude to performing the test, valve 286a is actuated to occlude inlet path 228a. The pump motor 272a is advanced a few steps to increase the pressure within the pumping chamber 230a to a predetermined level. Based upon both the relative position of the piston 240a and the measured chamber pressure, the fluid delivery system determines whether a sufficient quantity of fluid was delivered to the pumping chamber 230a. Third, a second fluid is introduced into the pumping chamber 230a through the synchronized operation of the inlet valves. Lastly, the accuracy of the total fluid volume is tested in accordance with the procedure above. Upon determining that the pump chamber has filled properly, the fill protocol is completed.

As should be gained from this operational description, the piston assembly 210 reduces the opportunity for damage to blood or blood-fluid mixtures in the pumping process. Specifically, the pump assembly 210 does not possess those features that facilitate the trapping of blood in or about the pumping chamber 230 or subject the blood to damaging compressive forces (roller pumps) or shearing forces (centrifugal pumps).

From the relationship correlating piston position to pumping chamber volume, one will appreciate that various fluids may be mixed at definable ratios through simply controlling the number of steps the pumping motors 272a, 272b move for each fill stage. As well, the total volumetric flow rate delivered by the pump mechanism 130 is dependent upon the user-defined flow rate.

Figure 12:
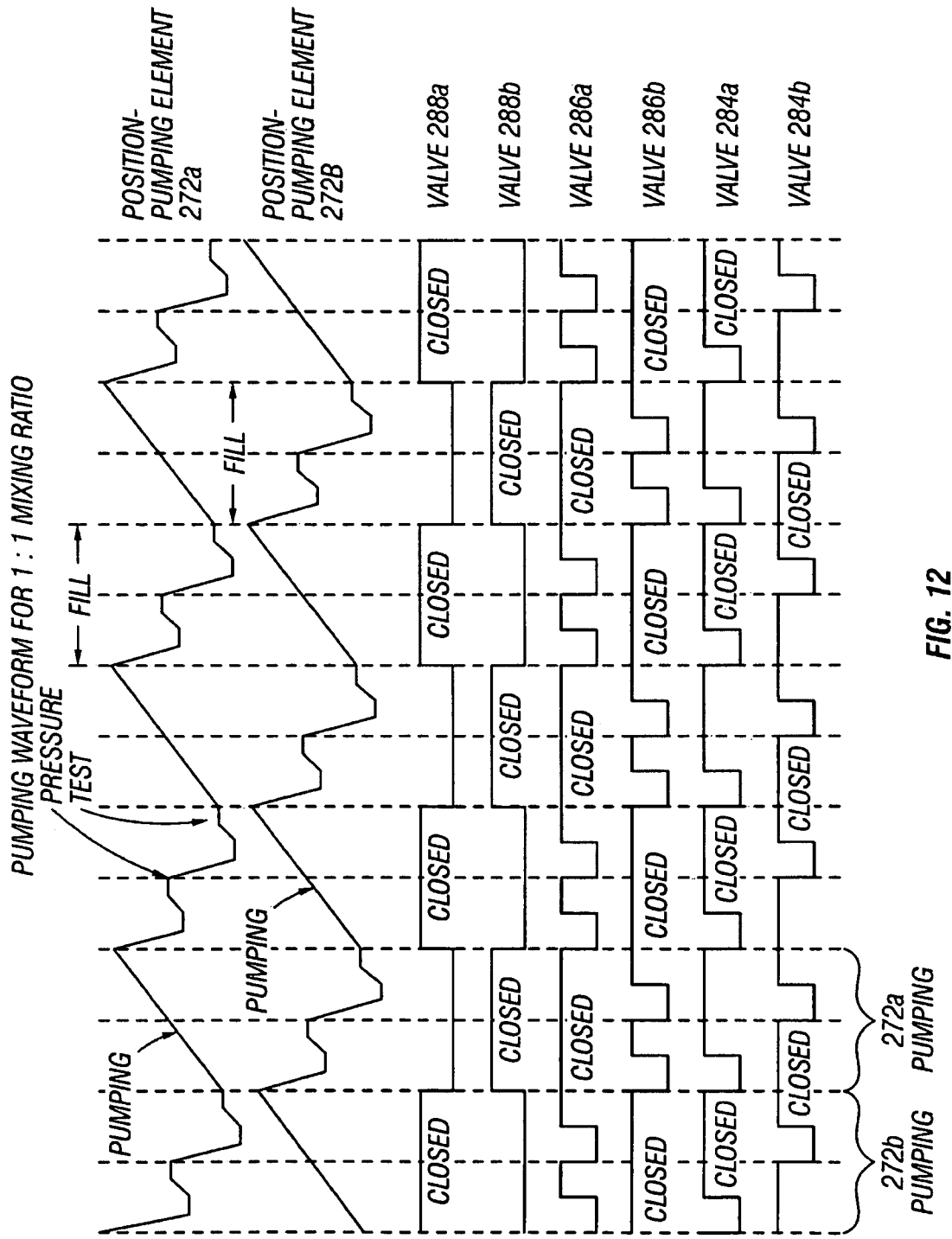
FIG. 12 is a timing diagram illustrating a cycle of the blood/crystalloid pump depicted in FIGS. 1-11 when operated in a non-pulsatile flow mode.

FIG. 12 illustrates a timing diagram for the operation of the valve cam motors 280 and 282 in conjunction with the pumping motors 272a and 272b. In the example cycle described, one chamber pumps a mixture of blood and crystalloid in a selected ratio outwardly from outlet 235 of cassette 220 (FIG. 3), while the other pumping chamber is undergoing a sequential fill and test protocol. The filling chamber is filled with blood to the volume to produce the desired ratio followed by pressure testing of the chamber with its inlet and outlet valves closed to verified capture of the desired amount of blood. Following this step, the drive element of the filling pumping chamber is further retracted and crystalloid solution admitted to complete the filling of the chamber. Then the inlet and outlet valves on the filling chamber are closed to pressure test the chamber for a captured full load. Additional pressure tests and monitoring may be conducted during pumping to determine if there is any unsafe occlusion or to control the pressure within an appropriate safe range for a given procedure.

Thus, at the commencement of the FIG. 12 diagram, the pumping chamber bladder 230a has been emptied, and the other bladder 230b is full of a blood-crystalloid mixture in the desired proportions. The outlet valve 288a, from chamber 230a is closed. Outlet valve 288b is open to pass the combined fluid from chamber 230b through the outlet 235 to the heat exchanger 131 (see FIG. 1) at the requested volumetric flow rate. Throughout the period of delivery from chamber 230b, its inlet valve 286b remains closed, and the corresponding piston 240b is advanced by motor 272b to reduce the volume of bladder 230b to expel the blood/crystalloid solution. The speed of motor 272b is governed by the requested flow rate. The outlet valve 288a from chamber 230a remains closed throughout this period of pumping from chamber 230b.

The valves 284a and 284b controlling inlet of blood and crystalloid to common inlet path 226, and the inlet valve for chamber 230a (inlet valve 286a) are sequentially opened and closed during the filling protocol for bladder 230a, which occupies the time period during which bladder 230b is delivering fluid to line 128 (see FIG. 1). Thus, when one bladder has completed its pumping step, the other has received solution constituents in the desired ratio and is ready to deliver, thereby enabling substantially continuous flow.

In the 4-step filling protocol for chamber 230a, illustrated at the outset of the diagram, valves 284a and 286a are initially open, and valve 284b closed. Thus, an open flow path for entry of blood to chamber 230a is provided through inlet 222, common inlet path 226, and pump chamber inlet path 228a, while crystalloid is occluded at valve 284b. Pump motor 272a (shown in FIG. 2) is retracted sufficiently to admit sufficient blood to comprise the desired fraction of total chamber volume. Then valves 284a and 286a are closed, and pump motor 272a is advanced a few steps, to confirm by elevating pressure that the requested blood load has been captured between closed valves 286a and 288a.

With confirmed introduction of the correct amount of blood, valves 286a and 284b are opened while valve 284a remains closed to stop further blood entry. Pump motor 272a now retracts to admit the correct volume of crystalloid along paths 225, 226 and 228a. This is followed by closing valves 286a and 284b. Motor 272a is advanced briefly to confirm by pressure elevation that the full incremental volume has been occupied by crystalloid solution. With this confirmation, the fill protocol is complete, and chamber 230a is ready for delivery on the completion of delivery from chamber 230b. As chamber 230a then delivers, chamber 230b undergoes a similar 4-step filling protocol.

The total volumetric flow rate from the cassette is varied pursuant to operator request simply by compressing or expanding the time for a cycle to be completed. Of course, if intermittent operation is desired, this may be provided as well. No matter what changes may be made to the blood/crystalloid flow rate, microprocessor 146 preferably automatically controls potassium pump 132 to deliver at a concentration which provides the requested potassium concentration.

Figure 13:
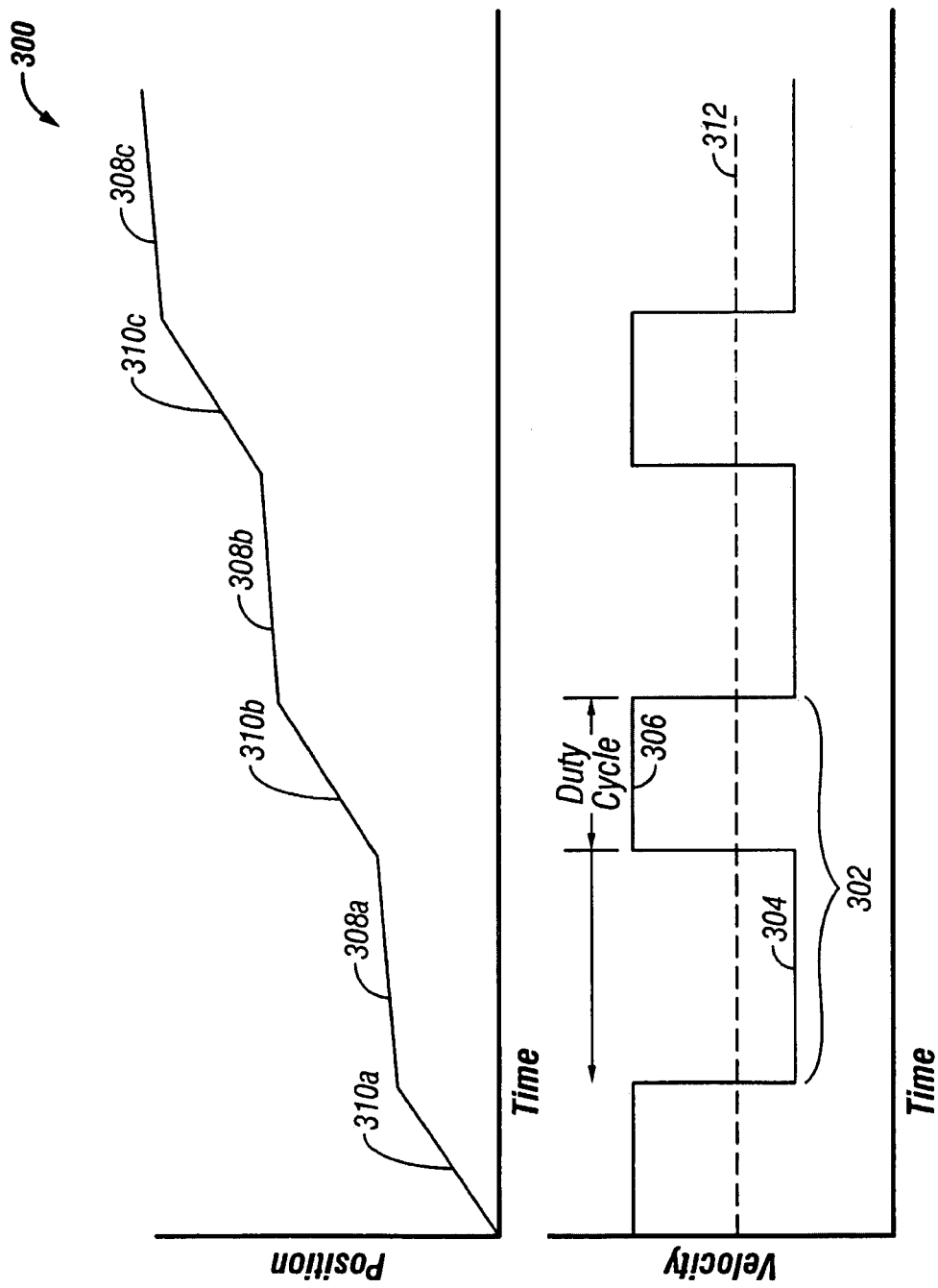
FIG. 13 is a timing diagram illustrating a cycle of the blood/crystalloid pump depicted in FIGS. 1-11 when operated in a pulsatile flow mode in accordance with a * preferred embodiment of the present invention.

Turning now to FIG. 13, a timing diagram illustrating the operation of a preferred embodiment of the present invention in a pulsatile flow mode is depicted. Timing diagram 300 shows position and velocity of a single piston, such as piston 240a while pumping the contents of its pumping chamber out. In a preferred embodiment, because spline pistons are utilized, the flow rate of the fluid leaving the pumping chamber is related quadratically to the velocity of the piston. To achieve a pulsatile flow, the velocity of the piston is varied cyclically. Period 302 represents one cycle of this cyclic flow characteristic. While the slopes of 310a, 310b, and 310c appear substantially equal, it is likely that the actual slope would be steeper for 310b and 310c due to the non-linear nature of the surface area of the piston being applied to the fluid pouch as the piston is advanced.

Period 302 comprises a partial-cycle 304 during which the piston is moved at a lower velocity, so as to achieve a lower flow rate. During a second partial-cycle 306, the piston is moved at a higher velocity, thus achieving a higher flow rate. The proportion of period 306 during which the higher velocity is applied to period 302 is referred to as the "duty cycle" of period 302. As shown in FIG. 13, this velocity characteristic (which also represents the instantaneous flow rate) is a square- or rectangle-wave. Due to compliance in the tubing connecting the cardioplegia delivery system to the patient, the actual flow rate characteristic and actual fluid pressure characteristic experienced by the patient is more sinusoidal in nature. It should also be noted that the flow rate(s) so obtained have the desirable property of being independent of the fluid pressure of the fluid being pumped. A desirable fluid pressure, for physiological purposes, is within the range of 50-250 mmHg.

The upper and lower velocities, corresponding to upper and lower flow rates, respectively, are selected so as to achieve a desired average flow rate over time given a particular amplitude and duty cycle for the pulsatile flow. The difference in pressure obtained during the upper flow rate and that obtained during the lower flow rate is called the "pulse pressure." An operator may also specify a particular frequency, corresponding to a simulated heart rate, at which the operator wishes the pulsatile flow to run. In order to simulate normal physiological conditions, a frequency of between 50-90 beats per minute is typically used. As shown in FIG. 13, the position of the piston varies at a low rate of change 308 during the low-velocity portion of period 302, while the position changes at a higher rate 310 during the high-velocity portion of period 302. Although the instantaneous velocity of the piston, and hence the instantaneous flow rate of the fluid being pumped, changes from instant-to-instant, the average rate of flow over time is a constant and is the same as would be achieved using a non-pulsatile flow, as indicated by dashed line 312 in FIG. 13.

As explained above, in the preferred embodiment of the present invention, the spline piston included a contact pressure sensor that permits monitoring of fluid pressure within a pumping chamber associated with the piston. As the piston engages the constrained, flexible cassette containing blood and/or other fluids, the pressure sensor is used to assess whether an adequate input volume was received in order to maintain a user specified output flow rate. If inadequate input volume is received into the first chamber, the operator is notified of the problem and has the option to correct the limitation or reduce the output flow rate.

Figure 14:
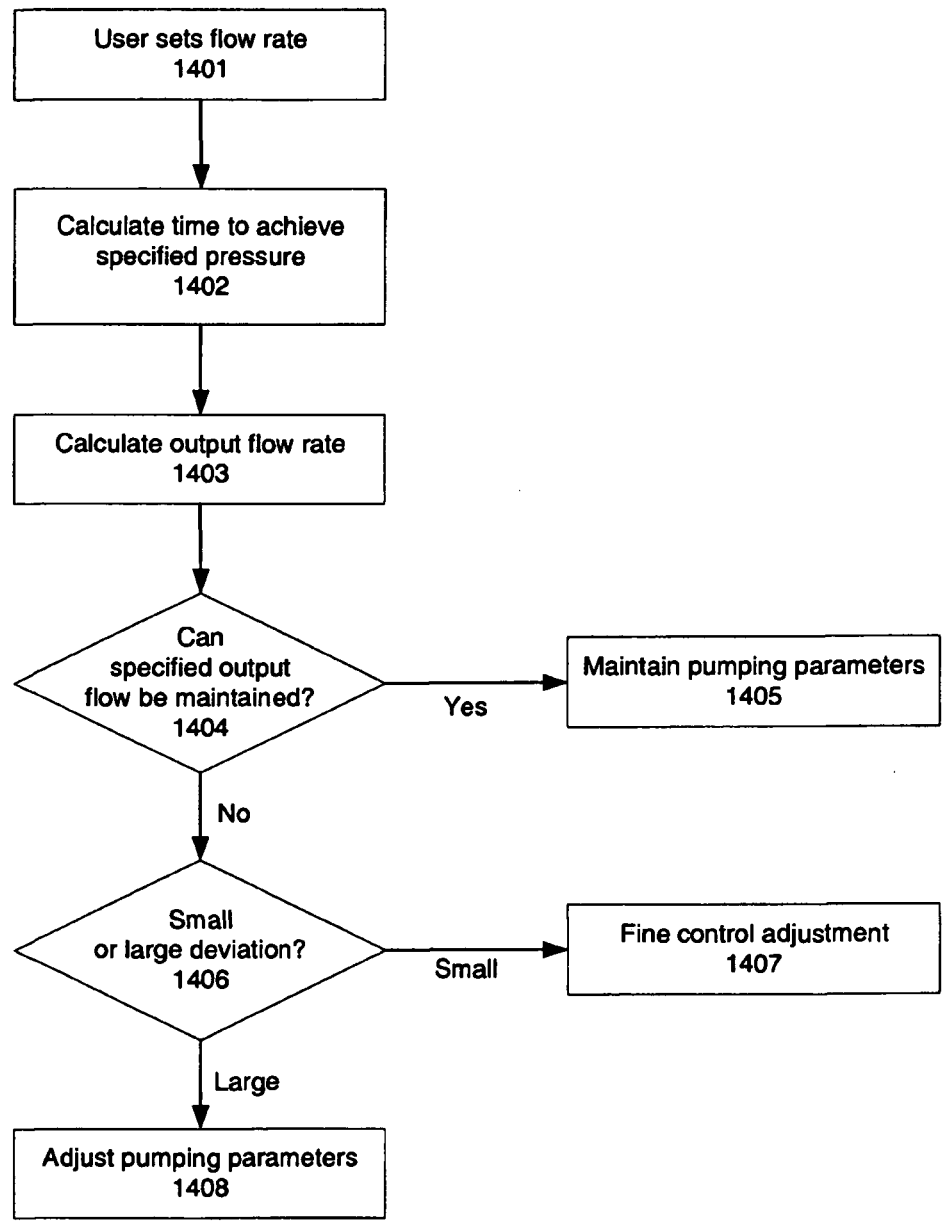
FIG. 14 is a flowchart illustrating the process of adapting output flow rate in accordance with a preferred embodiment of the present invention.

FIG. 14 is a flowchart illustrating the process of adapting output flow rate in accordance with a preferred embodiment of the present invention. The invention utilizes the pressure sensor information from the pistons and adapts the output flow rate to match the input flow rate.

A user initially sets the desired flow rate for the pump (step 1401). At the end of each pump cycle, a microprocessor calculates the time taken to achieve a specified pressure at the end of the refill period (step 1402). This data is then used to calculate the output flow rate (step 1403).

The microprocessor compares the output flow rate of the previous pump cycle to a pre-set target value range to determine if the specified output flow can be maintained (step 1404). If so, the pump parameters are maintained at their current levels (step 1405).

If the specified target output flow cannot be maintained, the microprocessor then determines if the output flow rate of the previous pump cycle has made a small or large deviation from the specified target (step 1406). For example, a small deviation may be defined as an output flow within +10% of the specified output flow rate, which would require only slight adjustments to the pumping parameters. In this same example, any deviation greater than +10% of the specified output flow rate would be considered a large deviation.

If the deviation from the specified output flow rate is small, the microprocessor instructs the piston pump motor to make fine control adjustments to its flow rate relative to available input (step 1407). Fluid output rate can be adjusted either by increasing or decreasing piston velocity (stroke rate), by changing stroke volume, or a combination of the two methods.

If the deviation from the specified output flow rate is large, the microprocessor instructs the piston motor pump to make large increment adjustments to its flow rate relative to the available input flow rate (step 1408). Large increment adjustments are needed to bring the output flow rate close to the input flow rate in as little time as possible to minimize the time during which large deviations occur. In such situations, fine control adjustments would be unable to bring the output flow rate closer in line with the input flow rate within the necessary time frame (the next pump cycle).

For example, if the output flow rate of the previous pump cycle deviated from the specified rate by 40% (e.g., the output flow was only 60% of what it should have been), the microprocessor will instruct the pump to make a large increment adjustment to the pumping parameters in an attempt to get the output flow rate closer to the input flow rate on the next pump cycle. Several large increment adjustments may be needed before the microprocessor switches to fine control.

The microprocessor adjusts the output flow rate for each pump cycle.

The range of flow rates fall within operator-set constraints such that the operator is notified in the event the input flow cannot support the minimum output flow rate, or conversely, if the input rate supports a flow rate above the specified maximum output flow rate.

One embodiment of the present invention enables the sterile cassette to be refilled with a second fluid as a means to increase the circulating volume and thereby increase the pressure in the patient, increasing the flow rate returning from the patient to the pump.

The present invention can be constructed in single-pump or multiple-pump configurations.

The adaptive piston-pump of the present invention prevents excessive negative pressures in the pump inlet conduit and the patient's venous system. If further coupled with a second fluid input capability, the invention can infuse the specific fluid volumes for supporting an output flow rate that maintains a patient's arterial blood pressure within a prescribe range.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

I claim:

1. A self-adjusting fluid pump for circulating fluid through an extracorporeal path, comprising:
    (a) a piston pump containing at least one piston and piston motor, said piston including a pressure sensor;
    (b) a flexible cassette with at least one fluid input containing one or more fluids, adjacent to said piston, wherein advancing the piston causes said one or more fluids to flow from the cassette to a patient and wherein said cassette has a plurality of inlet valves that communicate with a first and second pumping chamber;
    (c) a processing means for using data from the piston pressure sensor to calculate the rate of fluid input flow into each respective pumping chamber for each pump cycle, and to calculate an output flow rate based upon the input flow rate;
a second fluid input is coupled to the cassette to infuse a calculated volume for supporting the calculated output flow rate to maintain a patient's arterial blood pressure within a prescribed range;
    wherein
    said processing means is configured to compare said calculated output flow rate from part (c) to a pre-specified target output flow rate; and
    said processing means is configured to implement a filling protocol into said first pumping chamber in parallel to the expulsion of said one or more fluids from said second pumping chamber, said filling protocol further comprising:
    (1) synchronizing the plurality of inlet valves to introduce a first fluid into said first pumping chamber by retracting said piston motor a predefined amount to admit a volumetric quantity of the first fluid relative to the total volume of said first pumping chamber;
    (2) testing the volumetric accuracy of the first fluid within said first pumping chamber by occluding an inlet path to said first pumping chamber, advancing said piston motor to increase the pressure within said first pumping chamber to a predetermined level, and determining whether a sufficient quantity of the first fluid was delivered to said first pumping chamber based on the relative position of said piston and the measured pressure in said first pumping chamber;
    (3) synchronizing the plurality of inlet valves to introduce a second fluid into said first pumping chamber; and
    (4) testing the volumetric accuracy of the total volume of fluid within said pumping chamber by occluding the inlet path to said first pumping chamber, advancing said piston motor to increase the pressure within said first pumping chamber to a predetermined level, and determining whether a sufficient quantity of first and second fluids was delivered to said first pumping chamber based on the relative position of said piston and the measured pressure in said first pumping chamber.

2. The fluid pump according to claim 1, wherein the flexible cassette is formed from two flexible sheets of material, wherein the sheets are bonded together along a selected bond area to form particularized open flow paths and said first and second pumping chambers.

3. The fluid pump according to claim 2, wherein the flexible sheets are made of polyvinylchloride.

4. The fluid pump according to claim 1, wherein the piston is a spline piston.

5. The fluid pump according to claim 1, wherein the step of calculating the rate of fluid input flow in part (c) further comprises calculating the time taken to achieve a specified fluid pressure at the end of a refill period.

6. The fluid pump according to claim 1, wherein the fluid output flow rate from the fluid pump is influenced by a fluid input rate from venous return from a patient.

7. The fluid pump of claim 1 wherein the output flow rate is adjustable by said processing means adjusting piston velocity, stroke volume, or a combination of both.

8. The fluid pump according to claim 7, wherein an error range for determining whether a deviation is large or small is defined as when the measured ouput flow rate deviates by ten percent from the target output flow rate, wherein if the deviation is larger than ten percent, said deviation is defined as large.

9. The fluid pump according to claim 8, wherein if the deviation from the target output flow rate is large, the processing means makes large increment adjustments to the output flow rate to bring output flow within said pre-determined error range and then switches to fine control adjustments within said error range.

10. The fluid pump according to claim 9, wherein large increment adjustments to the output flow rate constitute adjustments of ten percent or more.

11. The fluid pump according to claim 1, wherein the processing means adjusts the output flow rate for each pump cycle.

12. The fluid pump according to claim 1, wherein the target output flow rate falls within operator constraints, wherein the operator is notified if input flow Cannot support a minimum output flow rate, or conversely, if input flow supports an output flow rate above a specified maximum.

13. The fluid pump according to claim 1, wherein the second fluid is added to the flexible cassette as a means to increase circulating volume and thereby increase input flow rate returning from a patient to the pump.

14. The fluid pump according to claim 1, further comprising multiple pistons and corresponding fluid pump chambers.

\* \* \* \* \*

UNITED STATES PATENT AND TRADEMARK OFFICE
CERTIFICATE OF CORRECTION

PATENT NO.        : 8,475,138 B2               Page 1 of 1
APPLICATION NO.   : 12/199669
DATED             : July 2, 2013
INVENTOR(S)       : Jones It is certified that error appears in the above-identified patent and that said Letters Patent is hereby corrected as shown below:

On the Title Page, Item [57]:
Line 7, please delete "till" and insert --fill--.
Line 8, please delete the "," after --microprocessor--.

In the Drawings:
Figure 3, top center, right side of figure, please change reference numeral 238b to 288b.
Figure 3, top center bottom of figure, please change reference numeral 238a to 288a.

In the Specification:
Column 2, Line 18, please delete the duplicate "of the piston" after --of the piston--.
Column 2, Line 37, please delete "*" before --preferred--.

Column 7, Line 14, please delete "236b" and replace with --230b--.

Column 10, Line 48, please delete "+" and insert --±-- before 10%.
Column 10, Line 51, please delete "+" and insert --±-- before 10%.

In the Claims:
Column 13, Line 5, claim 12, please delete "operator" and insert --operator-set--.
Column 13, Line 6, claim 12, please delete "Cannot" and insert --cannot--.

Signed and Sealed this
Eleventh Day of March, 2014

Michelle K. Lee
*Deputy Director of the United States Patent and Trademark Office*